United States Patent [19]

Maruya et al.

[11] Patent Number: 4,781,915
[45] Date of Patent: Nov. 1, 1988

[54] COSMETIC

[75] Inventors: Yoshiji Maruya, Tokyo; Toshio Taki, Kanagawa, both of Japan

[73] Assignee: Sogo Pharmaceutical Company Limited, Sagamihara, Japan

[21] Appl. No.: 803,822

[22] Filed: Dec. 2, 1985

Related U.S. Application Data

[63] Continuation of Ser. No. 522,457, Aug. 9, 1983, abandoned.

[30] Foreign Application Priority Data

Aug. 26, 1982 [JP] Japan ................................. 57-146898

[51] Int. Cl.$^4$ .......................... A61K 7/40; A61K 7/42; A61K 7/48
[52] U.S. Cl. ....................................... 424/59; 424/62; 514/844; 514/938
[58] Field of Search ............................. 424/59, 60, 62

[56] References Cited

FOREIGN PATENT DOCUMENTS 58-134022  7/1983  Japan ................................. 424/319
1308434    2/1973  United Kingdom ............... 424/319

OTHER PUBLICATIONS

Nakamura et al., Japan J. Microbiology, 1972, vol. 16(3), pp. 239–242.

Primary Examiner—Dale R. Ore
Attorney, Agent, or Firm—Browdy and Neimark

[57] ABSTRACT

A cosmetic comprising pantetheine-S-sulfonic acid and/or its salt. A pantetheine-S-sulfonate can prevent pigmentation on the skin. The present invention provides a cosmetic having an extremely high beautifying effect.

2 Claims, 1 Drawing Sheet

COSMETIC

BACKGROUND OF THE INVENTION

This application is a continuation of applicaton Ser. No. 522,457, filed Aug. 9, 1983, now abandoned.

This invention relates generally to a cosmetic and more particularly, to a beautifying cosmetic which is prepared by blending pantetheine-S-sulfonic acid and-/or its salt with a cosmetic base and which has pleasant feel and high preservability.

Pantetheine-S-sulfonic acid and its salts are known as effective compounds as a precursor of coenzyme A which plays an important role in energy metabolism, lipid metabolism and acetylation in organisms (Japan. J. Microbiol. Vol. 16 (3), 239–242 (1972)). However, the use of the acid or salt as a cosmetic, especially as a cosmetic having a particularly high beautifying effect, has not at all been realized in the past.

Hydrogen peroxide, ascorbic acid, colloidal sulfur and the like have been mostly used in the field of cosmetics, particularly to obtain a beautifying effect. However, these compounds are not entirely satisfactory because of their low stability, offensive odor and handling as well as because of their effect. Therefore, it has been an urgent problem in the cosmetic industry to develop a material which can replace these compounds.

To solve the problem described above, the inventor of the present invention has carried out a series of screening tests on a large number of organic and inorganic compounds which have known and unknown structures and are used not only in the field of cosmetics but also in the fields of pharmaceuticals and industrial chemicals and has come to realize that pantothenic acid is a compound of specific interest. The inventor has furthered his studies on the compounds of pantothenic acid type and has found that pantetheine-S-sulfonic acid has a remarkably high action of beautifying the skin on the basis of tyrosinase activity inhibition. The present invention is completed on the basis of this finding.

Pantetheine-S-sulfonic acid or its salt is a known compound represented by the following formula:

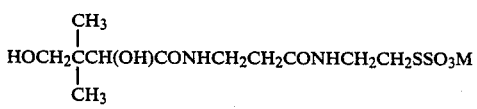

where M is hydrogen, alkali metal or 1/2 alkaline earth metal. Since this acid or salt can be easily mass-produced from D-pantothenic acid and 2-aminoethanethiol sulfate, the problem of supply of the effective ingredient no longer exists.

Pantethine and pantetheine can be cited as the compounds that are relatively analogous to pantetheine-S-sulfonic acid but these compounds have critical problems as a material for cosmetics. For example, pantethine is a non-crystalline viscous substance and is extremely inconvenient to handle as a cosmetic. When prepared as a product, it is sticky and does not provide a satisfactory feel. Moreover, it does not have any remarkable beautifying effect as will become more obvious from the Test Examples which will be described later. For these reasons, pantethine can not be used as a material for cosmetics. On the other hand, pantetheine has extremely strong odor and from this aspect, it can never be used as a material for cosmetics, to say nothing of its use as a material for beautifying cosmetics.

In contrast, pantetheine-S-sulfonic acid has an extremely high beautifying effect as will become apparent from the Test Examples, and is a powder which is odorless and easy to handle. Moreover, it is by far more economical than the two compounds described above.

SUMMARY OF THE INVENTION

On the basis of the novel finding described above and as a result of further studies, the inventor of this invention has confirmed that pantetheine-S-sulfonic acid has excellent miscibility and compatibility with a cosmetic base and with other blend components and is also excellent as a cosmetic base. Thus, the present invention provides a beautifying cosmetic characterized by comprising pantetheine-S-sulfonic acid and/or its salt.

A . . . test solution A,
B . . . test solution B,
C . . . comparative solution B,
D . . . blank.

Figure 2:
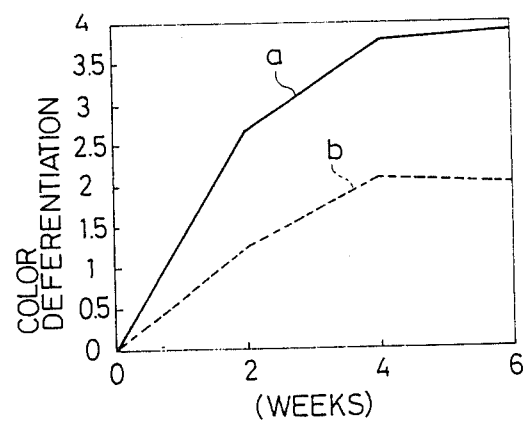

FIG. 2 is a diagram showing the clinical effect of creams, to which 10% and 0% of calcium pantetheine-S-sulfonate was blended, respectively, for chloasma in terms of changes in the average value of color difference with time. In the drawing, symbols have the following meaning, respectively:

a . . . cream to which 10% of calcium pantetheine-S-sulfonate was blended.
b . . . cream to which 0% of calcium pantetheine-S-sulfonate was blended.

DESCRIPTION OF THE PREFERRED EMBODIMENTS

When pantetheine-S-sulfonic acid and/or its salt as the effective ingredient of the present invention is blended, it may be used either alone or in combination of the both and further in combination with other beautifying materials. Though the acid or salt is used as a cosmetic material, it is not limited by cosmetic bases used. In other words, animal and vegetable fats (oils), higher alcohols, glycols, surfactants, pigments, perfumes, stabilizers, and other components that have been used generally as the cosmetic base can be used freely. The blend amount of the acid or its salt is generally from 0.1 to 50% (by weight), though the value is not limitative, in particular.

The cosmetic of the present invention can be prepared by any conventional method employed in the art. Hereinafter, the present invention will be described in further detail with reference to Test Example 1 which evidences that pantetheine-S-sulfonic acid and/or its salt has a tyrosinase activity inhibiting action, Test Example 2 which evidences the beautifying effect when the cosmetic of the invention is applied in practice to the skin, Test Example 3 which illustrates comparative tests using a color and color difference meter, and Examples of the present invention.

TEST EXAMPLE 1

0.25 g and 0.625 g (0.0083 mol) of calcium pantetheine-S-sulfonate were dissolved each in 100 ml of water to prepare test solutions A and B. Separately, a pantethine solution at the same molar rate as the test solution B was prepared (0.43 g/100 ml as a comparative solution B. The following tests were conducted using these test solutions and comparative solution.

0.9 ml each of the test solutions and comparative solution was placed in a test tube with 1 ml of an L-tyrosine solution (0.3 mg/ml) and 1 ml of a McIlvaine buffer solution (pH 6.8) and was incubated at 37° C. for 10 minutes. After 0.1 ml of a tyrosinase solution (1 mg/ml) was added to each solution, the mixture was stirred and its absorbancy was immediately measured at 475 nm with the passage of time using a spectrophotometer. As a blank test, the same procedures as described above were followed using water in place of the test and comparative solutions described above.

Figure 1:
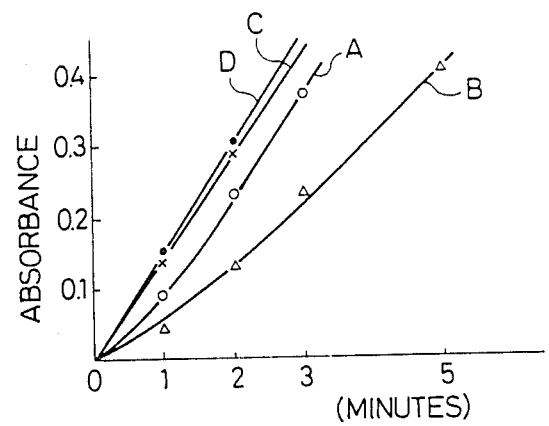
FIG. 1 is a diagram showing that calcium pantetheine-S-sulfonate has an extremely high tyrosinase activity inhibiting action in the Test Example 1, and symbols in the drawing have the following meaning, respectively.

The results were shown in FIG. 1. It could be found out from FIG. 1 that whereas calcium pantetheine-S-sulfonate inhibited the tyrosinase activity in any concentration, pantethine did not exhibit any inhibiting effect at all.

TEST EXAMPLE 2

Beauty wash in accordance with the present invention (having the recipe described in Example 1 which follows) and beauty wash containing ascorbic acid (1%) as a blend were respectively applied every morning and evening for three months to groups of subjects, each consisting of seven subjects suffering from chloasma, melanosis, ephelides and the like. The results were shown in Table 1.

TEST EXAMPLE 3

Changes in the difference of lightness between pigmented and non-pigmented portions were measured using a color and color difference meter (Model CP6R, a product of Nippon Denshoku K.K.). Measurement was carried out by a half side test in the following manner.

A cream containing 10% of calcium pantetheine-S-sulfonate as a blend was applied to either of the right and left halves of the face of each of nine patients suffering from chloasma as an example of pigmentation and a cream not containing calcium pantetheine-S-sulfonate, to the other half. Each cream was applied daily (once a day). (The absence of the irritating effect of the creams was confirmed in advance by a patch test.)

The results are shown in Table 2 and FIG. 2. Numeric values are the differences between the color differentiation (non-pigmented portion−pigmented portion) before and after the remedy, and the greater the values, the greater the effect of improvement.

It was found clearly from Table 2 that when the cream containing 10% of calcium pantetheine-S-sulfonate was applied daily, the numeric value became progressively greater with time, thus indicating that the improving effect for the chloasma was high. As to the mean value, too, the effect of the cream of the invention was obviously higher than that of the cream not containing the sulfonate as shown in FIG. 2. Significant differences were also found by the t-test at the fourth week ($P=0.035<0.05$) and at the sixth week ($P=0.096<0.1$). It was clarified from all these results that the cream containing 10% of calcium pantetheine-S-sulfonate was extremely effective clinically for the pigmentation, especially the chloasma.

TABLE 2

Clinical effect of 10% calcium pantetheine-S—sulfonate for chloasma (numeric value representing color differentation

| Case No. | 10% | | | | 0% | | | |
|---|---|---|---|---|---|---|---|---|
| | 0 | 2 weeks later | 4 weeks later | 6 weeks later | 0 | 2 weeks later | 4 weeks later | 6 weeks later |
| 1 | 0.0 | 3.3 | 7.0 | 6.5 | 0.0 | 4.7 | 3.5 | 5.8 |
| 2 | 0.0 | 2.6 | 1.6 | 4.2 | 0.0 | −1.1 | −1.1 | −0.4 |
| 3 | 0.0 | 4.7 | 4.8 | | 0.0 | 3.7 | 5.0 | |
| 4 | 0.0 | 2.1 | 1.9 | 5.2 | 0.0 | 1.0 | 1.4 | 2.5 |
| 5 | 0.0 | 1.9 | | −0.5 | 0.0 | 1.4 | | 0.0 |
| 6 | 0.0 | −1.3 | | | 0.0 | −2.0 | | |
| 7 | 0.0 | 6.6 | 3.4 | | 0.0 | 2.0 | 1.6 | |
| 8 | 0.0 | 5.3 | | | 0.0 | 6.0 | | |
| 9 | 0.0 | −1.1 | | | 0.0 | 4.6 | | |
| M | 0.0 | 2.67 | 3.74 | 3.85 | 0.0 | 1.23 | 2.08 | 1.975 |

TABLE 1

Result of Beautifying Tests

| | Beautifying effect | | | |
|---|---|---|---|---|
| | extremely good | good | no change | bad |
| Cosmetic of this invention | 2 | 5 | 0 | 0 |
| Cosmetic containing acorbic acid | 0 | 3 | 4 | 0 |

As a result, it was found that the cosmetic of the present invention was by far superior to the cosmetic containing ascorbic acid as a blend in the aspect of the beautifying effect.

The following are examples of beauty cosmetics in accordance with the present invention and numerical values represent wt %.

EXAMPLE 1

Beauty Wash

| | | |
|---|---|---|
| 1. | ethanol | 5.0 |
| 2. | vegetable oil | 0.1 |
| 3. | POE hydrogenated castor oil | 0.5 |
| 4. | propylene glycol | 5.0 |
| 5. | calcium pantetheine-S—sulfonate | 1.0 |
| 6. | antiseptic and perfume | suitable amounts |
| 7. | purified water | q.s. to 100 ml |

Components 1, 2 and 3 were dissolved and were then added to a mixed solution of components 4 through 7 to prepare a product.

EXAMPLE 2

| Beauty pack | | |
| --- | --- | --- |
| 1. | polyvinyl alcohol | 20.0 |
| 2. | ethanol | 20.0 |
| 3. | propylene glycol | 3.0 |
| 4. | sodium pantetheine-S—sulfonate | 0.5 |
| 5. | antispetic and perfume | suitable amounts |
| 6. | purified water | q.s. to 100 g |

Component 2 was wetted in component 1 and was added to water 6 dissolving therein the rest of the components while the mixture was being heated. The components were dissolved with stirring to prepare a product.

EXAMPLE 3

| Beauty cream (O/W type) | | |
| --- | --- | --- |
| 1. | vaseline | 2.5 |
| 2. | liquid paraffin | 10.0 |
| 3. | cetostearyl alcohol | 12.0 |
| 4. | polyoxyethylene sobitan monostearate | 7.0 |
| 5. | sorbitan monostearate | 1.0 |
| 6. | propylene glycol | 5.0 |
| 7. | calcium pantetheine-S—sulfonate | 1.0 |
| 8. | antiseptic and perfume | suitable amounts |
| 9. | purified water | q.s. to 100 ml |

The oil layer of components 1 through 5 and the aqueous layer of components 6, 8 and 9 were heated to 75° C. and emulsified. Component 7 was added in the course of cooling and the mixture was cooled down to 30° C. to prepare a product.

EXAMPLE 4

| Beauty lotion | | |
| --- | --- | --- |
| 1. | microcrystalline wax | 1.0 |
| 2. | beeswax | 2.0 |
| 3. | lanolin | 2.0 |
| 4. | liquid paraffin | 28.0 |
| 5. | sorbitan sesquioleate | 4.0 |
| 6. | Tween 80 | 1.0 |

| -continued | | |
| --- | --- | --- |
| Beauty lotion | | |
| 7. | aluminum stearate | 0.2 |
| 8. | glycerol | 8.0 |
| 9. | sodium pantetheine-S—sulfonate | 1.0 |
| 10. | antiseptic and perfume | suitable amounts |
| 11. | purified water | q.s. to 100 ml |

The oil layer of components 1 through 7 and the aqueous layer of components 8, 10 and 11 were heated to 70° C. and emulsified. Component 9 was added in the course of cooling and the mixture was cooled down to 30° C. to prepare a product.

What is claimed is:

1. A cosmetic preventing pigmentation on the skin, said cosmetic being prepared by blending 0.1–50% of pantetheine-S-sulfonic acid salt represented by the following formula:

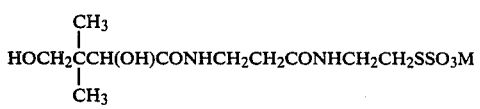

where M is alkali metal or ½ alkaline earth metal, with a cosmetically acceptable base comprising a member selected from the group consisting of animal fat, vegetable fat, higher alcohols, glycols and mixtures thereof and a member selected from the group consisting of surfactants, pigments, stabilizers and mixtures thereof.

2. A method of preventing pigmentation on the skin, comprising the step of applying on the skin a cosmetic preventing pigmentation on the skin, said cosmetic being prepared by blending 0.1–50% of pantetheine-S-sulfonic acid salt represented by the following formula:

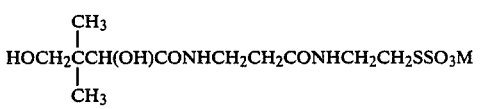

where M is alkali metal or ½ alkaline earth metal, with a cosmetically acceptable base comprising a member selected from the group consisting of animal fat, vegetable fat, higher alcohols, glycols and mixtures thereof and a member selected from the group consisting of surfactants, pigments, stabilizers and mixtures thereof.

* * * * *